US009880162B2

(12) United States Patent
Kim et al.

(10) Patent No.: US 9,880,162 B2
(45) Date of Patent: Jan. 30, 2018

(54) METHOD FOR MANUFACTURING MULTI-FUNCTIONAL BIO-MATERIAL CONJUGATE USING TWO KINDS OF PARTICLE, AND MULTI-FUNCTIONAL BIO-MATERIAL CONJUGATE MANUFACTURED BY MEANS OF SAME

(71) Applicants: GWANGJU INSTITUTE OF SCIENCE AND TECHNOLOGY, Gwangju (KR); KOREA RESEARCH INSTITUTE OF BIOSCIENCE AND BIOTECHNOLOGY, Daejeon (KR)

(72) Inventors: Min-Gon Kim, Daejeon (KR); Yun Ju Sung, Daejeon (KR); Ju Young Byun, Daejeon (KR); Young-Kyoung Oh, Gwangju (KR); Hyou-Arm Joung, Gwangju (KR)

(73) Assignees: GWANGJU INSTITUTE OF SCIENCE AND TECHNOLOGY, Gwangju (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 139 days.

(21) Appl. No.: 14/351,291

(22) PCT Filed: Oct. 12, 2012

(86) PCT No.: PCT/KR2012/008301

§ 371 (c)(1),
(2) Date: Apr. 11, 2014

(87) PCT Pub. No.: WO2013/055142

PCT Pub. Date: Apr. 18, 2013

(65) Prior Publication Data

US 2014/0272945 A1 Sep. 18, 2014

(30) Foreign Application Priority Data

Oct. 14, 2011 (KR) ........................ 10-2011-0105463

(51) Int. Cl.
*G01N 33/543* (2006.01)
*B82Y 40/00* (2011.01)
(Continued)

(52) U.S. Cl.
CPC ........ *G01N 33/54346* (2013.01); *B82Y 40/00* (2013.01); *G01N 33/54333* (2013.01);
(Continued)

(58) Field of Classification Search
CPC ................................................ G01N 33/54346
(Continued)

(56) References Cited

U.S. PATENT DOCUMENTS

| | | | | |
|---|---|---|---|---|
| 2003/0082237 | A1* | 5/2003 | Cha et al. | 424/490 |
| 2009/0117002 | A1 | 5/2009 | Kotov et al. | |

FOREIGN PATENT DOCUMENTS

| | | | |
|---|---|---|---|
| KR | 20010058711 | A | 7/2001 |
| KR | 20090116142 | A | 11/2009 |

(Continued)

OTHER PUBLICATIONS

Bai et al., "Ultrasensitive electrochemical detection of DNA hybridization using Au/Fe3O4 magnetic composites combined with silver enhancement," The Royal Society of Chemistry, May 24, 2010, vol. 135, pp. 1672-1679.*

(Continued)

*Primary Examiner* — Tracy Vivlemore
*Assistant Examiner* — Nam P Nguyen
(74) *Attorney, Agent, or Firm* — Hauptman Ham, LLP

(57) ABSTRACT

Disclosed herein are a method for manufacturing a multi-functional bio-material conjugate used as a biosensor for
(Continued)

detecting microorganisms, and the like, and a multi-functional bio-material conjugate manufactured by means of the same. The method for manufacturing a multi-functional bio-material conjugate includes: (a) coating a first nanoparticle having magnetic or fluorescent characteristics with protein; (b) manufacturing a conjugate by adsorbing a second nanoparticle having metallic characteristics onto the first nanoparticle coated with protein; and (c) manufacturing the multi-functional bio-material conjugate by adsorbing a bio-material onto the conjugate. The method for manufacturing a multi-functional bio-material conjugate according to the present invention may prevent precipitation of the nanoparticles, easily immobilize the bio-material, and manufacture a bio-material conjugate having multiple functions, by using two kinds of the particles. In addition, the multi-functional bio-material conjugate manufactured by the present method may be used to detect microorganisms at up to a concentration of $10^1$ cfu.

9 Claims, 15 Drawing Sheets

(51) Int. Cl.
*G01N 33/58* (2006.01)
*B82Y 15/00* (2011.01)
*G01N 33/569* (2006.01)

(52) U.S. Cl.
CPC ............ *G01N 33/587* (2013.01); *B82Y 15/00* (2013.01); *G01N 33/569* (2013.01); *Y10S 977/774* (2013.01)

(58) Field of Classification Search
USPC .......................................................... 436/501
See application file for complete search history.

(56) References Cited

FOREIGN PATENT DOCUMENTS

| | | | |
|---|---|---|---|
| KR | 100962286 | B1 | 6/2010 |
| KR | 20110058711 | A | 6/2011 |
| WO | 0045171 | A1 | 8/2000 |
| WO | 2011065747 | A2 | 6/2011 |

OTHER PUBLICATIONS

Mikhaylova et al., "BSA Immobilization on Amine-Functionalized Superparamagnetic Iron Oxide Nanoparticles," Chem. Mater., 16, 2344-2354, published 2004.*
Brewer et al., Probing BSA Binding to Citrate-Coated Gold Nanoparticles and Surfaces, Langmuir, 21, 9303-9307, published 2005.*
Choi et al., Kr 100962286 (machine translation), published Jun. 11, 2010.*
Lloyd et al., "Protein Structure and Protein Hydration", pp. 132-146, published on Jan. 1, 1933.*
Nel et al.,"Understanding biophysicochemical interactions at the nano-bio interface", Nature Materials, vol. 8, pp. 543-557, published Jul. 2009.*
Zhuo et al., "Functionalized SiO2 labeled CA19-9 antibodies: A new strategy for signal amplification of antigen-antibody sensing processes", vol. 135, pp. 2036-2042, published Jun. 3, 2010.*
O Cespedes et al., "Contact induced magnetism in carbon nanotubes", Journal of Physics Condensed Matter, vol. 16, pp. L155- L161, published Feb. 27, 2004.*
Pan et al. ("How Do Proteins Unfold upon Adsorption on Nanoparticle Surfaces", Langmuir, 2012, vol. 28, 12779-12787.*
Wang et al., "Magnetic Nanoparticle-Enhanced Biosensor Based on Grating-Coupled Surface Plasmon Resonance", Anal. Chem., vol. 83, pp. 6202-6207, published Jun. 28, 2011.*
Yu-Hui Bai et al., Ultrasenstive Electrochemical Detection of DNA Hybridization Using Au/Fe3O4 Magnetic Composites Combined With Silver Enhancement, article, published as an advance article on the web May 24, 2010, pp. 1672-1679, The Royal Society of Chemistry 2010.
Zhifeng Zhang et al., Preparation and Application of Streptavidin Magnetic Particles, article, Feb. 2007, pp. 127-134, vol. 50, No. 1.
International Search Report for PCT/KR2012/008301 dated Mar. 13, 2013, citing the above reference(s).
Chinese Office Action dated Apr. 16, 2015, citing the above reference(s).

* cited by examiner

BEFORE AMPLIFICATION OF GOLD (Au) NANOPARTICLE

80nm MNP($Fe_2O_3$)-Au-CRP Ab 90nm MNP($Fe_3O_4$-$SiO_2$)-Au-CRP Ab

METHOD FOR MANUFACTURING MULTI-FUNCTIONAL BIO-MATERIAL CONJUGATE USING TWO KINDS OF PARTICLE, AND MULTI-FUNCTIONAL BIO-MATERIAL CONJUGATE MANUFACTURED BY MEANS OF SAME

CROSS REFERENCE TO RELATED APPLICATION

This application claims the priority of Korean Patent Application 10-2011-0105463 filed on Oct. 14, 2011 in the Korean Patent and Trademark Office. Further, this application is the National Phase application of International Application No. PCT/KR2012/008301 filed on Oct. 12, 2012, which is incorporated herein by reference in its entirety.

TECHNICAL FIELD

The present invention relates to a method for manufacturing a multi-functional bio-material conjugate, and a multi-functional bio-material conjugate manufactured by means of the same, and more specifically, to a method for manufacturing a multi-functional bio-material conjugate used as a biosensor for detecting microorganisms, and the like, and a multi-functional bio-material conjugate manufactured by means of the same.

BACKGROUND ART

Nano- and micro-sized particles to which bio-materials are bound have been applied to biosensing, bioimaging, isolation, and the like, in various fields such as food, health care, diagnosis, and life science. For example, an antibody-magnetic nanoparticle conjugate and an antibody-gold nanoparticle have been used for detecting a target material by a bond between an antigen and an antibody in an immune sensor (Yu-Hui Bai. et al., *Anal.* 135:1672-1679, 2010).

One of factors having a significant effect on formation of an antigen-antibody reaction conjugate is an antibody immobilization method, and therefore, various immobilization technologies have been developed, and there are various methods for binding protein. For example, there are a method using chemical and physical adsorption, a method for binding protein to a gold nanoparticle using cystein which is an amino acid specifically bound to gold, a method for producing a monomolecular film on a gold nanoparticle and then covalently binding protein to the gold nanoparticle using a functional group of the monomolecular film, and a method for adsorbing avidin protein on a surface of the gold nanoparticle and binding protein to which biotin is bound (ZHANG zhiFeng et al., *Sci china ser B-Chem.* 50(1):127-134, 2007), and the like.

However, currently developed immobilization technology according to the related art has problems in that conditions of immobilization reaction such as pH are varied depending on properties of protein, and in a case of a nanoparticle, dispersion is not achieved but nanoparticles are flocculated.

Korean Patent No. 0962286 discloses a magnetic core gold nanoparticle for detecting food-borne pathogens, a manufacturing method thereof, and a detecting method of food-borne pathogens using the nanoparticle, which is characterized by including: preparing a magnetic body core containing magnetic materials; modifying a surface of the magnetic body core with an amine functional group; and forming a gold particle layer on a surface of the magnetic body core surface-modified with the amine functional group.

However, the above-mentioned patent has problems in that reproducibility or efficiency of a chemical reaction generated at the time of modifying the surface of the magnetic body core with the amine functional group may be deteriorated and flocculation phenomenon in a solution may occur. In addition, significantly long reaction time is required for forming a gold particle layer, and food-borne pathogens enable to be detected only by a separate equipment, SPR, which is inconvenient.

Accordingly, the present inventors found that in a case of coating a first nanoparticle having magnetic or fluorescent characteristics with protein, manufacturing a conjugate by adsorbing a second nanoparticle having metallic characteristics onto the first nanoparticle, and adsorbing a bio-material onto the conjugate, precipitation of the nanoparticles may be prevented and the bio-material may be easily immobilized without performing an inconvenient modification process, and desired materials are capable of multi-functionally detected and isolated using properties of the protein coating the first nanoparticle and properties of the bio-material adsorbed onto the second nanoparticle, thereby completing the present invention.

SUMMARY OF THE INVENTION

An object of the present invention is to provide a bio-material conjugate capable of multi-functionally detecting or isolating desired materials, and a method for manufacturing the same.

Another object of the present invention is to provide a method for detecting microorganisms by a simplified method in a field.

According to an exemplary embodiment of the present invention, there is provided a method for manufacturing a multi-functional bio-material conjugate, the method including: (a) coating a first nanoparticle having magnetic or fluorescent characteristics with protein; (b) manufacturing a conjugate by adsorbing a second nanoparticle having metallic characteristics onto the first nanoparticle coated with protein; and (c) manufacturing the multi-functional bio-material conjugate by adsorbing a bio-material onto the conjugate.

According to another exemplary embodiment of the present invention, there is provided a multi-functional bio-material conjugate including: a first nanoparticle having magnetic or fluorescent characteristics and coated with protein, and a second nanoparticle having metallic characteristics and adsorbed onto the protein, wherein a bio-material is adsorbed onto the second nanoparticle.

According to another exemplary embodiment of the present invention, there is provided a biosensor including the multi-functional bio-material conjugate as described above.

According to another exemplary embodiment of the present invention, there is provided a method for rapidly detecting a microorganism using a multi-functional bio-material conjugate, the method including: (a) mixing the multi-functional bio-material conjugate with a sample containing a detection-target microorganism to prepare a reaction solution, the multi-functional bio-material conjugate including a first nanoparticle having magnetic or fluorescent characteristics and coated with protein, and a second nanoparticle having metallic characteristics and adsorbed onto the protein, wherein an antibody specifically bound to the detection-target microorganism is adsorbed onto the second nanoparticle; (b) sequentially passing the reaction solution through a film for flocculating microorganism and a filtration membrane for capturing microorganism to permeate a multi-functional bio-material conjugate which is not reacted with the microorganism, thereby selectively isolating a multi-functional bio-material conjugate-microorganism composite; and (c) measuring whether or not the multi-functional bio-material conjugate-microorganism composite captured in the filtration membrane for capturing microorganism is present or a concentration of the multi-functional bio-material conjugate-microorganism composite.

DESCRIPTION OF THE EXEMPLARY EMBODIMENTS

Figure 1:
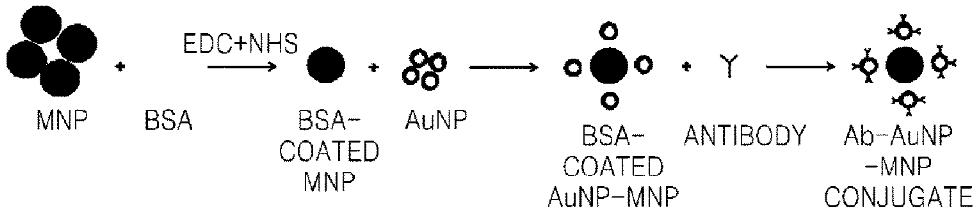
FIG. 1 shows a schematic view showing a method for immobilizing an antibody to a composite containing a magnetic nanoparticle and a gold nanoparticle according to the present invention.

The present invention confirmed that in a case where a conjugate is manufactured by coating protein with a first nanoparticle having magnetic or fluorescent characteristics and adsorbing a second nanoparticle having metallic characteristics onto the first nanoparticle and then a bio-material is adsorbed onto the conjugate, a multi-functional bio-material conjugate in which the bio-material is not flocculated and easily immobilized, and detection and analysis performance are capable of being improved by utilizing properties of protein and bio-material coating the first nanoparticle may be manufactured.

In the present invention, after the first nanoparticle having magnetic or fluorescent characteristics is coated with protein, the second nanoparticle having metallic characteristics is adsorbed onto the first nanoparticle coated with protein to thereby manufacture the conjugate, and then the bio-material is adsorbed onto the conjugate, thereby manufacturing a multi-functional bio-material conjugate.

That is, it was confirmed in an embodiment of the present invention that as a result of manufacturing BSA protein-coated magnetic nanoparticle (MNP)-gold nanoparticle (AuNP)-antibody and BSA protein-coated fluorescent latex beads (LB)-silver nanoparticle (AgNP) or gold nanoparticle (AuNP)-antibody, an immobilization efficiency of the antibodies was excellent, and using the antibodies, *Staphylococcus aureus* was capable of being detected with excellent sensitivity.

Therefore, according to an exemplary embodiment of the present invention, there is provided a method for manufacturing a multi-functional bio-material conjugate, the method including: (a) coating a first nanoparticle having magnetic or fluorescent characteristics with protein; (b) manufacturing a conjugate by adsorbing a second nanoparticle having metallic characteristics onto the first nanoparticle coated with protein; and (c) manufacturing the multi-functional bio-material conjugate by adsorbing a bio-material onto the conjugate.

In addition, according to another exemplary embodiment of the present invention, there is provided a multi-functional bio-material conjugate including: a first nanoparticle having magnetic or fluorescent characteristics and coated with protein, and a second nanoparticle having metallic characteristics and adsorbed onto the protein, wherein a bio-material is adsorbed onto the second nanoparticle.

The first nanoparticle may have magnetic or fluorescent characteristics and, for example, may include latex, magnetic, silica, a quantum dot, a metal nanoparticle, and the like.

The second nanoparticle may have metallic characteristics and, for example, may include gold, silver, copper, platinum, and the like. It is preferred that the second nanoparticle favorably adsorbs protein.

Here, the term: "nanoparticle" refers to an ultra-fine particle having a size of about 1 nm to 100 nm. Nanoparticles having significantly small size have different characteristics from those of general flocculation materials. The nanoparticle has a remarkably increased specific surface area as compared to the existing materials. Due to the increased specific surface area, the nanoparticle has a different surface effect as compared to the existing materials, that is, as a size of the particle becomes decreased, the number of molecules positioned on the surface thereof are increased. In a case where the particle has a diameter of 5 nm, 50% of molecules consisting of the particle are positioned on a surface of the particle and in a case where the particle has a diameter of 2 nm, 90% of molecules are positioned on the surface thereof. Since a ratio of the molecules positioned on the surface thereof is relatively high, the nanoparticles have high ratio of a surface energy to a binding energy as compared the existing materials. The ratio of the surface energy to the binding energy becomes increased from 5% to about 30% as the size of the particle becomes decreased from 20 nm to 1 nm. Atoms consisting of the particles are placed at an energy steady state reaching balance between attraction and repulsion by an interaction between the atoms and atoms adjacent thereto. However, since the atoms positioned on the surface have only attraction by inner atoms, the atoms are placed at high energy state. Due to the surface effect, the nanoparticles have characteristics such as surface activity, decrease in a melting point, low-temperature sinterablity, and the like, shown in the catalyst or on the surface of the catalyst.

It is preferred that the first nanoparticle has a size larger than that of the second nanoparticle.

For example, the first nanoparticle has a size of 20 to 500 nm, and the second nanoparticle has a size of 5 to 100 nm.

In a case of using the first nanoparticle having a size larger than that of the second nanoparticle, a small nanoparticle enables to be easily adsorbed.

Protein coating the first nanoparticle is to easily immobilize a bio-material to be immobilized by using an adsorption characteristic without a modification process, and as the protein, BSA, peroxidase, alkaline phosphatase, glucose oxidase, choline oxidase, streptavidin, skim milk, serum, peptide, and the like, may be used.

That is, in a case of coating the first nanoparticle with protein as described above, the multi-functional bio-material conjugate is capable of being manufactured by the adsorption method using the second nanoparticle favorably adsorbing protein.

The bio-material may be selected from a group consisting of an antibody, an enzyme, DNA, an aptamer, a peptide nucleic acid (PNA), and a ligand.

According to another exemplary embodiment of the present invention, there is provided a biosensor including the multi-functional bio-material conjugate.

It could be confirmed in another embodiment of the present invention that a multi-functional bio-material conjugate is manufactured using an antibody specifically bound to microorganism as a bio-material, and the microorganism is capable of being detected at a high speed at the time of reacting the conjugate with the microorganism.

Therefore, according to another exemplary embodiment of the present invention, there is provided a method for rapidly detecting a microorganism using the multi-functional bio-material conjugate, the method including: (a) mixing the multi-functional bio-material conjugate with a sample containing a detection-target microorganism to prepare a reaction solution, the multi-functional bio-material conjugate including a first nanoparticle having magnetic or fluorescent characteristics and coated with protein, and a second nanoparticle having metallic characteristics and adsorbed onto the protein, wherein an antibody specifically bound to the detection-target microorganism is adsorbed onto the second nanoparticle; (b) sequentially passing the reaction solution through a film for flocculating microorganism and a filtration membrane for capturing microorganism to permeate a multi-functional bio-material conjugate which is not reacted with the microorganism, thereby selectively isolating a multi-functional bio-material conjugate-microorganism composite; and (c) measuring whether or not the multi-functional bio-material conjugate-microorganism composite captured in the filtration membrane for capturing microorganism is present or a concentration of the multi-functional bio-material conjugate-microorganism composite.

The film for flocculating microorganism, the filtration membrane for capturing membrane, the isolation method, and the measuring method, used in the method for rapidly detecting the microorganism may be used by referring to description of Korean Patent Laid-Open Publication No. 10-2011-0058711 previously filed by the present inventors.

For example, the film for flocculating microorganism may be selected from a group consisting of polydimethylsiloxane (PDMS), polymer and aluminum tape having adhesion, rubber and latex, and a paste for screen printing. Preferably, the film for flocculating microorganism may be a film manufactured by applying the paste for screen printing such as a silver paste or a carbon paste to the filtration membrane for capturing the microorganism, provided with holes having each predetermined size, using a screen printing method. Therefore, the film for flocculating microorganism and the filtration membrane for capturing the microorganism may be configured in an integrated type, and the screen printing method may be any well-known methods in the art.

As an example of the screen printing method, there is a method for fixing a screen mesh made of nylon, polyester or stainless steel, and the like, to frame made of wood, aluminum, and the like, forming a sheet membrane thereon by a handwork scheme or a photochemical scheme to close parts rather than required images, and filling a paste for screen printing thereinto, thereby passing the paste through the mesh not having the sheet membrane when applying pressure an inner portion of the screen by a spatula to move the paste, so that the paste passed through the mesh is printed onto a material to be printed, positioned under the sheet.

The filtration membrane for capturing microorganism has a pore size of 100 nm to 10 μm. The nanoparticle to which the antibody non-bound to microorganism is immobilized passes through the filtration membrane for capturing microorganism, and the microorganism non-bound to the nanoparticle having immobilized microorganism is not indicated as a signal even though the microorganism is captured in the filtration membrane for capturing microorganism. Therefore, only the microorganism bound to the nanoparticle having immobilized antibody shows unique color, fluorescence, and the like, of the nanoparticle having immobilized antibody on the filtration membrane for capturing microorganism.

In an exemplary embodiment of the present invention, the filtration membrane for capturing microorganism having a pore size of 1.2 μm is used, but the pore size thereof is not limited thereto, which is obvious to those skilled in the art. Preferably, the filtration membrane for capturing microorganism may have a pore size selected from 100 nm to 10 μm so as to capture the microorganism reacted with the nanoparticle having immobilized antibody.

The filtration membrane for capturing microorganism may be made of a material selected from a group consisting of nitrocellulose, polycarbonate, nylon, polyester, cellulose acetate, polysulfone and polyethanesulfone.

The step (b) of selectively isolating of the multi-functional bio-material conjugate may be performed by using vacuum, centrifugation, or absorption method.

In other words, when the nanoparticle-antibody-microorganism complex is filtered by the filtration membrane for capturing microorganism after passing through the film for flocculating microorganism, the conjugate may be selectively isolated by applying vacuum, performing centrifugation, or absorbing the conjugate in the filtration membrane.

The measuring step (c) may be performed using a CCD camera or absorbance.

EXAMPLE

Hereinafter, the present invention will be described in detail with reference to the following Examples. However, the following examples are only for exemplifying the present invention, and it will be obvious to those skilled in the art that the scope of the present invention is not construed to be limited to these examples.

Example 1

Manufacture of Magnetic Nanoparticle-Antibody Conjugate and Fluorescent Bead-Antibody Conjugate

Example 1-1

Magnetic Nanoparticle (MNP)-Protein: Bovine Serum Albumin (BSA)-Protein-Coated Magnetic Nanoparticle (MNP)-Gold Nanoparticle (AuNP)-Antibody A bovine serum albumin (BSA) solution (pH 7.4, dissolved into 10 mM phosphate buffer) was added to a magnetic nanoparticle (MNP) solution so as to have a final volume of 1 ml and mixed with together, and 10 mM N-hydroxysuccinnimide (NHS, Biacore Inc.) and 2 mM EDC(Biacore Inc.) were added to the mixture, and left for 30 minutes. 0.1 ml of 100 mM glycin solution (pH 7.4, dissolved into 10 mM phosphate buffer) was added to the mixture, and left for 30 minutes, and divided into each 200 μlm, followed by centrifugation at 4° C. and 6,000 rpm for 20 minutes to remove a supernatant therefrom. Then, 0.2 ml of a borate buffer (10 mM, pH 8.5) was added thereto and mixed with together, followed by centrifugation at 6000 rpm for 20 minutes to remove a supernatant therefrom. After the above-described process was repeated once again, 0.4 ml of 100 nm magnetic nanoparticle-BSA was added to 0.1% BSA (pH 8.8, dissolved into 10 mM sodium bicarbonate buffer) solution, thereby finally manufacturing BSA protein-coated magnetic nanoparticle.

As the magnetic nanoparticle solution, 100 μl of 100 nm magnetic nanoparticle solution (CMX, 25 mg/ml, Chemicell) having a matrix made of carboxymethyl-dextran, 60 μl of 100 nm magnetic nanoparticle solution (PAS, 50 mg/ml, Chemicell) having a matrix made of polyacrylic acid, 180 μg of 90 nm magnetic nanoparticle ($Fe_3O_4$, provided by Prof. Sangmin Jeon from Pohang University Science and Technology: POSTECH) and 430 μg of 90 nm magnetic nanoparticle ($Fe_3O_4$—$SiO_2$, provided by Prof. Sangmin Jeon from Pohang University Science and Technology: POSTECH) were used.

1 ml of 10 nm gold nanoparticle solution (BB International, borate buffer 10 mM, pH 8.5) concentrated by 5 times was added to the BSA protein-coated magnetic nanoparticle obtained by performing the centrifugation to remove the supernatant therefrom, thereby being subjected to adsorption for 30 minutes.

10 μg of anti-*Staphylococcus aureus* monoclonal antibody (anti-*S. aureus* mAb, Abcam) was added to each of 100 nm CMX and PAS magnetic nanoparticle solutions, having the adsorbed gold nanoparticle, and 10 μg of anti-C-reactive protein monoclonal antibody (anti-CRP mAb, Abcam) was added to 80 nm magnetic nanoparticle ($Fe_3O_4$) and 90 nm magnetic nanoparticle ($Fe_3O_4$—$SiO_2$) solution.

After 30 minutes, 0.1 ml of 10% bovine serum albumin (BSA) solution (pH 8.8, dissolved into 10 mM sodium bicarbonate buffer) was added thereto, and left for 30 minutes. The solution was divided into each 200 μl, followed by centrifugation at 4° C. and 5,500 rpm for 20 minutes to remove a supernatant therefrom, and 0.2 ml of 0.1% BSA solution was added thereto, followed by centrifugation at 5,000 rpm for 20 minutes to remove a supernatant therefrom. The above-described process was repeated once again, and finally, 0.4 ml of 0.1% BSA (pH 8.8, dissolved into 10 mM sodium bicarbonate buffer) solution was added to 100 nm magnetic nanoparticle (CMX, PAS)-gold nanoparticle-anti-*Staphylococcus aureus* monoclonal antibody, and 0.1 ml thereof was added to 80 nm and 90 nm magnetic nanoparticle ($Fe_3O_4$, $Fe_3O_4$—$SiO_2$)-gold nanoparticle-anti-C-reactive protein monoclonal antibody and mixed with together, followed by filtration with 0.45 μm syringe filter, and the filtrate was stored in fridge.

Example 1-2

Protein Coated Fluorescent or Undyed Latex Beads (LB)-Silver Nanoparticle (AgNP) or Gold Nanoparticle (AuNP)-Antibody 50 μl of latex bead surface-modified with a carboxylic acid was subjected to centrifugation at 4° C. and 5,000 rpm for 3 minutes to remove a supernatant therefrom. Coating the latex bead with BSA was performed as the same as Example 1-1 above. As the latex bead solution, 2 μm fluorescent latex bead (Sigma Co.) and 0.9 μm latex bead (undyed, Sigma Co.) were used.

1 ml of each of 20 nm silver nanoparticle solution (BB International, 10 mM borate buffer, pH 8.5) and 10 nm gold nanoparticle solution (BB International, 10 mM borate buffer, pH 8.5), each concentrated by 5 times, was added to 2 μm fluorescent latex bead coated with BSA, thereby being subjected to adsorption for 30 minutes, and 10 μg of anti-C-reactive protein polyclonal antibody (anti-CRP pAb, Abcam) was added thereto, and left for 30 minutes. 10 μg of each of anti-H1 monoclonal antibody (anti-H1 mAb, LS-BIO) and anti-H5 monoclonal antibody (anti-H5 mAb, Abcam) was added to only the fluorescent latex bead coated with the silver nanoparticle, and left for 30 minutes.

The fluorescent latex bead solution having the silver or gold nanoparticle adsorbed thereonto by the BSA protein was prepared by the same method as Example 1-1 above, and during the preparation, centrifugation was performed at 5000 rpm for 10 minutes, and syringe filtration was not performed, 0.4 ml of 0.1% BSA (pH 8.8, dissolved into 10 mM sodium bicarbonate buffer) solution was added to the mixture, and the reactant was stored in fridge.

Example 1-3

Manufacture of Horeradish Peroxidase (HRP)-Coated Gold Nanoparticle-Gold Nanoparticle Antibody Conjugate 0.1 ml of borate buffer (0.1 M, pH 8.5) and 10 μg anti-aldehyde activated HRP (Thermo) were added to 1 ml of 20 nm gold nanoparticle solution (BB International). After 30 minutes, the reactant was subjected to centrifugation at 4° C. and 12,000 rpm for 15 minutes to remove a supernatant therefrom. Centrifugation was performed again, and 1 ml of 15 nm gold nanoparticle solution (BB International) was added to the reactant, 0.1 ml of buffer (0.1M, pH 8.5) and then 10 μg of Troponin I monoclonal antibody (Abcam, detection antibody) were added thereto. After 1 hour, 0.2 ml of 0.1% BSA (pH 7.4, dissolved into 10 mM phosphate buffer) solution was added thereto and mixed with together (5×), and the obtained gold nanoparticle (AuNP)-antibody was stored in fridge.

Example 2

Manufacture of Antibody Conjugate of Metal Nanoparticle

Example 2-1

Manufacture of Gold Nanoparticle (AuNP)-Antibody 0.1 ml of borate buffer (0.1 M, pH 8.5) and 10 μg anti-C-reactive protein monoclonal antibody (anti-CRP mAb which is capture Ab, Abcam) were added to 1 ml of 20 nm gold nanoparticle solution (BB International).

After 30 minutes, 0.1 ml of 10% bovine serum albumin (BSA) solution (pH 8.8, dissolved into 10 mM sodium carbonate buffer) was added thereto, and left for 30 minutes. The solution was subjected to centrifugation at 4° C. and 10,000 rpm for 20 minutes to remove a supernatant therefrom. 0.2 ml of 0.1% BSA (pH 8.8, dissolved into 10 mM sodium carbonate buffer) solution was added to the reactant and mixed with together, followed by centrifugation at 10,000 rpm for 15 minutes to remove a supernatant therefrom. The above-described process was repeated once again, and finally, 0.2 ml of 0.1% BSA (pH 8.8, dissolved into 10 mM sodium carbonate buffer) solution was added thereto and mixed with together, and the obtained gold nanoparticle (AuNP)-antibody was stored in fridge.

Example 2-2

Manufacture of Silver Nanoparticle (AgNP)-Antibody 1 ml of borate buffer (0.1 M, pH 8.5) and 10 μg of anti-C-reactive protein monoclonal antibody (anti-CRP mAb which is capture Ab, Abcam) were added to 1 ml of 20 nm silver nanoparticle solution (BB International) and left for 30 minutes.

The silver nanoparticle solution having immobilized antibody was prepared by the same method as Example 2-1, and the silver nanoparticle (AgNP)-antibody was stored in fridge.

Example 3

Manufacture of Polydimethylsiloxane (PDMS) Film Having Holes

A PDMS solution (Sylgard 184A, Dow Corning, USA) and a curing agent (Sylgard 184B, Dow Corning, USA) were mixed at a ratio of 10:1 and poured on a flat patri dish having a diameter of 150 mm. In addition, air bubbles in the mixture were removed by a vacuum pump, and the reactant was cured at 60° C. for 24 hours. Then, the cured PDMS film was cooled at room temperature, and made 6 holes using a perforator having a diameter of 15 mm. As a result, it was confirmed that the PDMS film having holes was manufactured.

Comparative Example 1

Manufacture of Magnetic Nanoparticle (MNP)-Antibody Conjugate

After 10 mM Phosphate buffer (PB, pH 7.4) was added to a magnetic nanoparticle solution surface-modified with carboxylic acid so as to have a final volume of 1 ml and mixed with together, 10 mM N-hydroxysuccinnimide (NHS, Biacore Inc.), 2 mM EDC (Biocore Inc.), and 10 μg of antibody were added thereto and left for about 2 hours.

As the magnetic nanoparticle solution, 100 μl of 100 nm magnetic nanoparticle solution (CMX, 25 mg/ml, Chemicell) having a matrix made of carboxymethyl-dextran, 60 μl of 100 nm magnetic nanoparticle solution (PAS, 50 mg/ml, Chemicell) having a matrix made of polyacrylic acid were used, and as an antibody, anti-*Staphylococcus aureus* monoclonal antibody (anti-*S. aureus* mAb, Abcam) was added. Anti-H1 monoclonal antibody (anti-H1 mAb, LS-BIO) and anti-H5 monoclonal antibody (anti-H5 mAb, Abcam) were added to only 100 nm magnetic nanoparticle solution having a matrix made of carboxymethyl-dextran.

The magnetic nanoparticle solution having immobilized antibody was prepared by the same method as Example 1-1.

Comparative Example 2

Manufacture of Undyed Latex Bead (LB)-Antibody Conjugate

50 μl of 0.9 μm latex bead (Sigma Co.) surface-modified with a carboxylic acid was subjected to centrifugation at 4° C. and 5,000 rpm for 3 minutes to remove a supernatant therefrom. After 10 mM Phosphate buffer (PB, pH 7.4) was added to the latex bead so as to have a final volume of 1 ml and mixed with together, 10 mM N-hydroxysuccinnimide (NHS, Biacore Inc.), 2 mM EDC(Biocore Inc.), and 10 μg of anti-human CD3 Ab, BD were added thereto and left for 2 hours.

The latex bead solution having immobilized anti-human CD3 antibody was prepared by the same method as Example 1-2 above.

Experimental Example 1

Analysis of *Staphylococcus aureus* Using BSA Protein-Coated Magnetic Nanoparticle (MNP, matrix: CMX)-Gold Nanoparticle (AuNP)-Antibody Experimental Example 1-1

Confirmation of Immobilization Efficiency of Antibody Using Viable Cell Count

40 μl of each solution containing 10 μg/ml of MNP (CMX)-BSA, BSA protein-coated MNP(CMX)-AuNP-anti-*S. aureus* mAb prepared by Example 1-1 above and containing MNP(CMX)-anti-*S. aureus* mAb conjugate prepared by Comparative Example 1, 10 μl ($10^5$ cfu) of solution prepared by suspending *Staphylococcus aureus*(*S. aureus*) in PBS and 100 μl of PBS solution were mixed together, and gently shaken for 30 minutes. After 30 minutes, 100 μl of PBS solution was added thereto, then using magnetic at room temperature, magnetic nanoparticles were separated from the solution for about 3 minutes, and *S. aureus* complex reacted with the supernatant and each magnetic nanoparticle conjugate was collected.

100 μl of the collected *S. aureus* mixture containing the supernatant and magnetic nanoparticle conjugate was smeared on agar medium (trypticase soy broth (BD 211825) 3%, agar powder 2%) in a petri dish and incubated at 37° C. for 16 to 24 hours. After the incubation, an effect of the antibody immobilization method using the magnetic nanoparticle and the gold nanoparticle was confirmed by measuring viable cell count formed on the medium.

Figure 2:
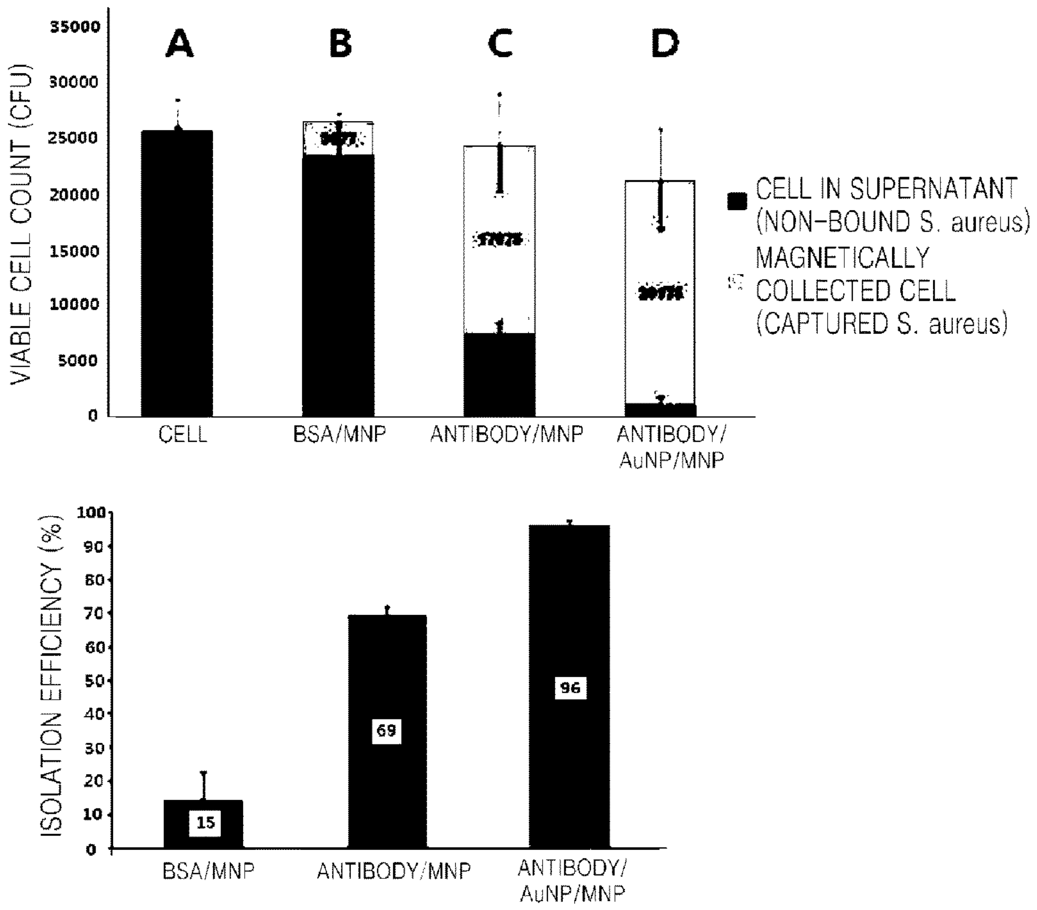
FIG. 2 is a graph showing viable cell counts measured from a conjugate from which *Staphylococcus aureus* of $10^5$ cfu is isolated and a supernatant, using MNP(CMX)-anti-*Staphylococcus aureus* mAb to which an antibody is immobilized without using a gold nanoparticle and MNP(CMX)-AuNP-anti-*Staphylococcus aureus* mAb to which an antibody is immobilized by using a gold nanoparticle (control(A), MNP-BSA(B), MNP-anti-*Staphylococcus aureus* mAb 10 ug/ml(C), BSA protein-coated MNP-5×AuNP-anti-*Staphylococcus aureus* mAb 10 ug/ml(D)+$10^5$ cfu *Staphylococcus aureus*)

As shown in FIG. 2, when using the BSA protein-coated magnetic nanoparticle (MNP)-gold nanoparticle (AuNP)-antibody conjugate, an antibody immobilization efficiency was increased by about 30% as compared to the method for directly immobilizing an antibody to a magnetic nanoparticle.

Experimental Example 1-2

Analysis of *Staphylococcus aureus*

A state in which the antibody of the manufactured magnetic nanoparticle conjugate was immobilized by the gold nanoparticle was confirmed by using the immobilization method according to the present invention. 10 μl of solution prepared by suspending *S. aureus* in PBS (100-5×$10^6$ cfu), 40 μl of BSA protein-coated MNP(CMX)-AuNP-anti-*S. aureus* mAb(Abcam) conjugate solution prepared by Example 1-1, and 50 μl of PBS solution were mixed together, and gently shaken for 30 minutes.

100 μl of PBS solution was added to the solution, then using magnetic, the magnetic nanoparticle was separated from the solution for about 3 minutes to remove a supernatant, and *S. aureus* reacted with BSA protein-coated MNP (CMX)-AuNP-anti-*S. aureus* mAb conjugate was collected.

As a filtration membrane for capturing microorganism, a nitrocelluolose (NC) film (Millipore) having a pore size of 1.2 μm obtained by applying 1% BSA solution (dissolved into PBS) thereto and performing a drying process was used. The NC film was placed onto a filter mounted in 100 μl of erlenmeyer flask having branches and the PDMS film manufactured by Example 3 above was covered onto the NC film. The mixture solution of *S. aureus* reacted with the collected BSA protein-coated MNP(CMX)-AuNP-anti-*S. aureus* mAb conjugate was allowed to pass through pores of the PDMS film by applying vacuum through branches of the flask, thereby confirming a concentration of *S. aureus*.

Figure 3:
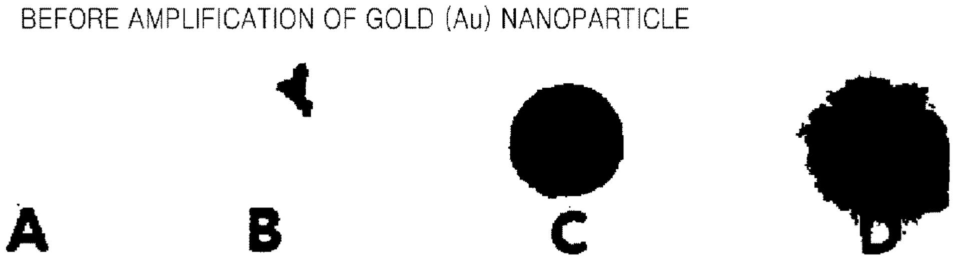
FIG. 3 shows results obtained by confirming an immobilization state of a conjugate for each concentration of *Staphylococcus aureus*, using BSA protein-coated MNP (CMX)-5×AuNP-anti-*Staphylococcus aureus* mAb according to an embodiment of the present invention ($10^0$ cfu(A), $5\times10^4$ cfu(B), $5\times10^5$ cfu(C), $5\times10^6$ cfu(D)+BSA protein-coated MNP(CMX)-5×AuNP-anti-*Staphylococcus aureus* mAb)

As a result, it was confirmed from FIG. 3 that the MNP(CMX)-AuNP-anti-*S. aureus* mAb conjugate in $10^0$ cfu *S. aureus* did not remain on the filtration membrane, and as a concentration of *S. aureus* became increased, an amount of the BSA protein-coated MNP(CMX)-AuNP-anti-*S. aureus* mAb conjugate remained on the filtration membrane was also increased. Therefore, it could be appreciated that microorganism bound to the magnetic nanoparticle having immobilization antibody due to the gold nanoparticle only remained on the filtration membrane for capturing microorganism, such that whether or not microorganism was formed and a concentration of the formed microorganism could be measured by the naked eye using unique color of the nanoparticle.

Experimental Example 1-3

Analysis of *Staphylococcus aureus* through Amplification of Gold Nanoparticle 10 mM citrate buffer (pH 3.0) containing 5 mM hydroxyl amine and 25 mM hydrogen tetrachloroaurate(III) was dropped onto the filtration membrane for capturing microorganism filtering the complex of *S. aureus* reacted with BSA protein-coated MNP(CMX)-AuNP-anti-*S. aureus* mAb conjugate of Experimental Example 1-2, and reacted at room temperature for about 15 minutes.

Figure 4:
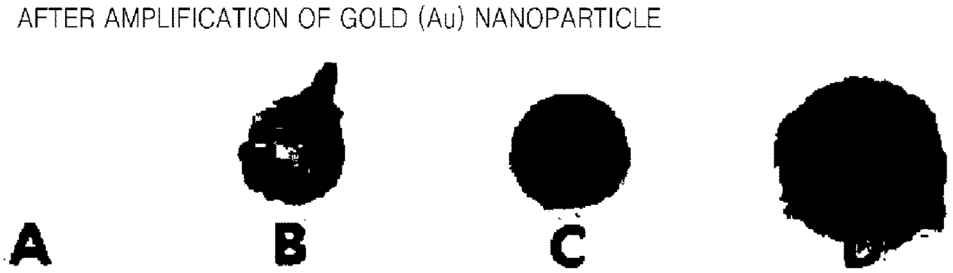
FIG. 4 shows results obtained by confirming an immobilization state of the conjugate (FIG. 3) through amplification of a gold nanoparticle for each concentration of *Staphylococcus aureus*, using the conjugate manufactured by using an immobilization method according to the present invention ($10^0$ cfu(A), $5\times10^4$ cfu(B), $5\times10^5$ cfu(C) and $5\times10^6$ cfu(D)+BSA protein-coated MNP(CMX)-5×AuNP-anti-*Staphylococcus aureus* mAb)

As a result, as shown in FIG. 4, it could be appreciated that sensitivity in measuring microorganism for each concentration was capable of being increased due to a bathochromic effect of BSA protein-coated MNP(CMX)-AuNP-anti-*S. aureus* mAb conjugate on the filtration membrane, obtained by reducing gold using a gold reduction solution.

Experimental Example 2

Analysis of *Staphylococcus aureus* Using BSA Protein-Coated Magnetic Nanoparticle (MNP, Matrix: PAS)-Gold Nanoparticle (AuNP)-Antibody and Confirmation of Cross-Reaction with Other Microorganism Experimental Example 2-1

Analysis of *Staphylococcus aureus*

A concentration of *S. aureus* was confirmed according to the same procedure as Experimental Example 1-2 above, using the BSA protein-coated MNP(PAS)-AuNP-anti-*S. aureus* mAb conjugate having a matrix made of polyacrylic acid conjugate by Example 1-1 above.

Figure 5:
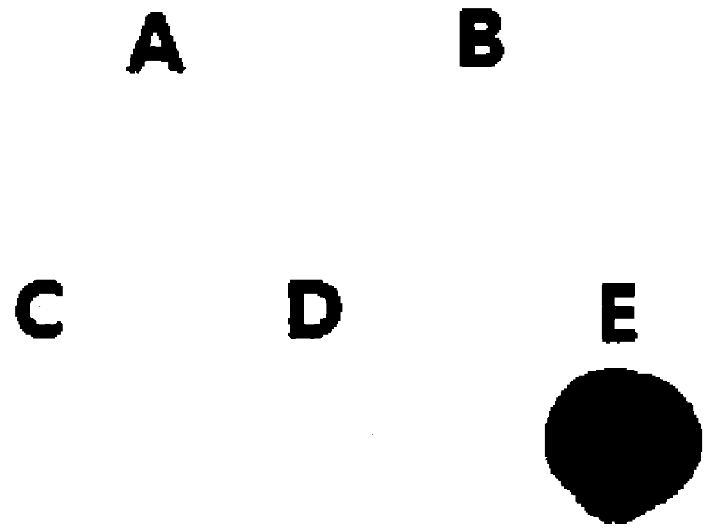
FIG. 5 shows results obtained by measuring *Staphylococcus aureus* for each concentration using BSA protein-coated MNP(PAS)-5×AuNP-anti-*Staphylococcus aureus* Ab according to an embodiment of the present invention ($10^0$ cfu(A), $5\times10^4$ cfu(B), $1\times10^5$ cfu(C)$5\times10^5$ cfu(D) and $5\times10^6$ cfu(E)+BSA protein-coated MNP(PAS)-5×AuNP-anti-*Staphylococcus aureus* mAb)

As a result, as shown in FIG. 5, the MNP(PAS)-AuNP-anti-*S. aureus* mAb conjugate having the matrix made of polyacrylic acid showed similar tendency to FIG. 3, and whether or not the microorganism was formed and a concentration of the formed microorganism could be measured using unique color of the nanoparticle having immobilized antibody.

Experimental Example 2-2

Figure 6:
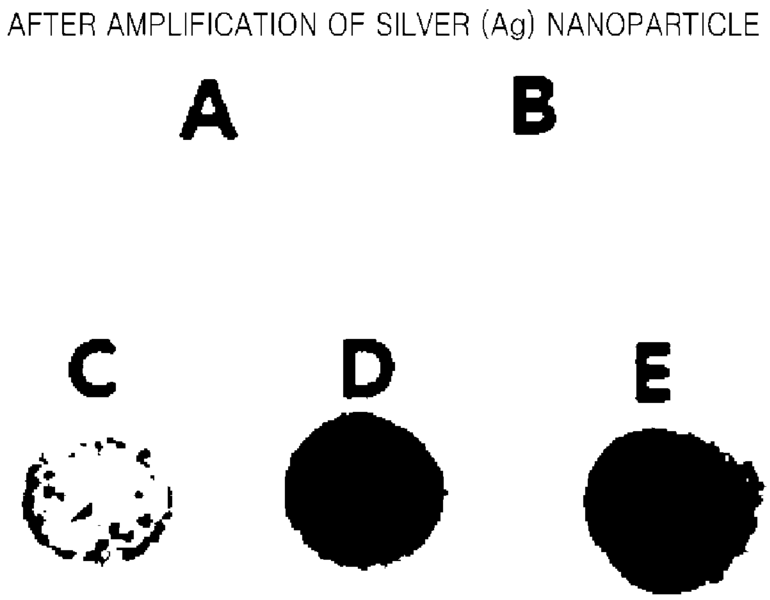
FIG. 6 shows results obtained by measuring *Staphylococcus aureus* for each concentration through amplification of a silver nanoparticle of the product of FIG. 5 ($10^0$ cfu(A), $5\times10^4$ cfu(B), $1\times10^5$ cfu(C)$5\times10^5$ cfu(D) and $5\times10^6$ cfu(E)+BSA protein-coated MNP(PAS)-5×AuNP-anti-*Staphylococcus aureus* mAb)

Analysis of *Staphylococcus aureus* through Amplification of Silver Nanoparticle A mixture for amplifying silver nanoparticle was prepared by mixing A (silver salt) solution and B (hydroquinone initiator) solution at a ratio of 1:1, and the mixture was dropped onto the filtration membrane for capturing microorganism of Experimental Example 2-1, and reacted at room temperature for about 10 minutes. As a result, as shown in FIG. 6, as a concentration of *S. aureus* became increased, sensitivity in measuring microorganism for each concentration was capable of being increased due to a bathochromic effect of BSA protein-coated MNP(CMX)-AuNP-anti-*S. aureus* mAb conjugate on the filtration membrane, through the amplification of silver nanoparticle.

Experimental Example 2-3

Confirmation of Cross-Reaction with Other Microorganism

In order to confirm whether or not the multi-functional bio-material conjugate according to the present invention enables to selectively detect microorganism, an experiment was performed using BSA protein-coated MNP(PAS)-AuNP-anti-*S. aureus* mAb, and by the same procedure as Experimental Example 2-1 above except for changing a kind of the microorganism. 4 different kinds of microorganisms, that is, *Salmonella typimurium, Listeria monocytogenes, Staphylococcus aureus, Escherichia coli*, were reacted with the MNP(PAS)-AuNP-anti-*S. aureus* mAb and then analyzed.

Figure 7:
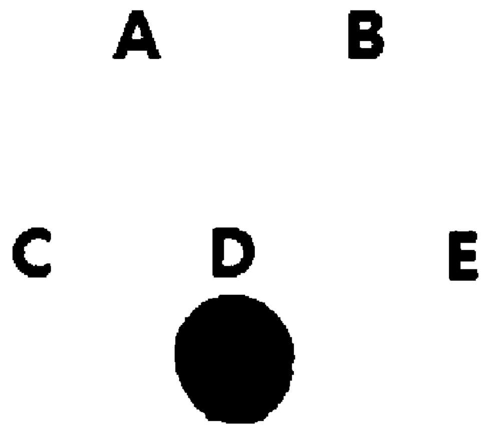
FIG. 7 shows results obtained by confirming whether or not a cross-reaction is generated with other microorganism with respect to BSA protein-coated MNP(PAS)-5×AuNP-anti-*Staphylococcus aureus* mAb ($10^0$ cells (A), $5\times10^5$ cfu *Salmonella* cells (B), $5\times10^5$ cfu *Listeria monocytogenes* cells (C), $5\times10^5$ cfu *S. aureus* cells (D) and $5\times10^5$ cfu *E. coli* cells (E)+MNP(PAS)-5×AuNP-anti-*Staphylococcus aureus* mAb)

As a result, it could be confirmed from FIG. 7 that in *Salmonella typimurium, Listeria monocytogenes* and *Escherichia coli*, BSA protein-coated MNP(PAS)-AuNP was not shown, and in *Staphylococcus aureus*, BSA protein coated MNP(PAS)-AuNP was selectively shown.

Experimental Example 2-4

Comparison of Immobilization Capacity of Antibody with *Staphylococcus aureus*

A conjugate manufactured by directly immobilizing anti-*S. aureus* mAb to MNP(PAS), that is, MNP(PAS)-anti-*S. aureus* mAb conjugate, and the BSA protein-coated magnetic nanoparticle (MNP, PAS)-gold nanoparticle (AuNP)-anti-*S. aureus* mAb conjugate were measured for each concentration by the same procedure as Experimental Example 2-1 above and compared by the naked eye.

Figure 8:
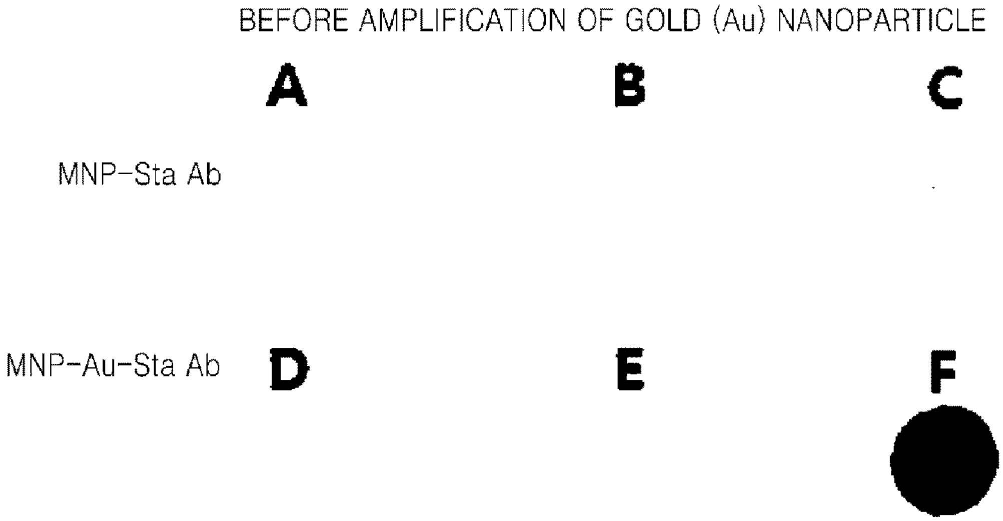
FIG. 8 shows results obtained by measuring *Staphylococcus aureus* for each concentration, using MNP(PAS)-anti-*Staphylococcus aureus* mAb to which an antibody is immobilized without using a gold nanoparticle and BSA protein-coated MNP(PAS)-5×AuNP-anti-*Staphylococcus aureus* mAb, to which an antibody is immobilized by using a gold nanoparticle ($10^0$ cfu(A,D), $5\times10^5$ cfu(B,E), $5\times10^6$ cfu(C, F)+MNP(PAS)-anti-*Staphylococcus aureus* mAb, BSA protein-coated MNP(PAS)-5×AuNP-anti-*Staphylococcus aureus* mAb)
Figure 9:
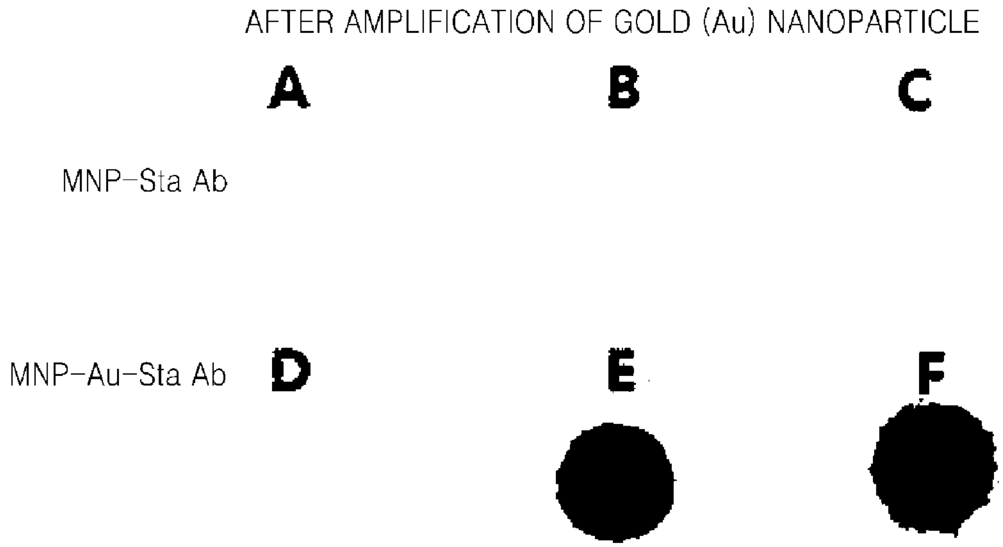
FIG. 9 shows results obtained by measuring *Staphylococcus aureus* for each concentration through amplification of a gold nanoparticle of the product of FIG. 8 ($10^0$ cfu(A,D), $5\times10^5$ cfu(B,E), $5\times10^6$ cfu(C,F)+MNP(PAS)-anti-*Staphylococcus aureus* mAb, BSA protein-coated MNP(PAS)-5×AuNP-anti-*Staphylococcus aureus* mAb)

As shown in FIG. 8, a signal was increased due to red color of the gold nanoparticle in the conjugate having immobilized antibody by BSA protein-coated magnetic nanoparticle (MNP, PAS)-gold nanoparticle (AuNP) as compared to the conjugate in which an antibody is directly immobilized to MNP(PAS), and as shown in FIG. 9, an increased signal was obtained by amplification of silver nanoparticle.

Experimental Example 3

CRP Measurement Using BSA Protein-coated Fluorescent Latex Bead (Fluorescent Yellow-green, LB)-Silver Nanoparticle (AgNP) or Gold Nanoparticle (AuNP)-Antibody Experimental Example 3-1

CRP Measurement through Fluorescent Signal

1 μl of BSA protein-coated fluorescent latex bead (fluorescent yellow-green, 2 μm LB)-silver nanoparticle, 20 nm AgNP)-anti C-reactive protein polyclonal antibody (anti-CRP pAb) conjugate and BSA protein-coated fluorescent latex bead (fluorescent yellow-green, 2 μm LB)-gold nanoparticle (20 nm AuNP)-anti C-reactive protein polyclonal antibody (anti-CRP pAb) conjugate, each 0, 1 μg/ml and 10 μg/ml of CRP antigens, and 10 μl of each of the gold nanoparticle (20 nm AuNP)-anti C-reactive protein monoclonal antibody (anti-CRP mAb) conjugate manufactured by Example 2-1 above or the silver nanoparticle (20 nm AgNP)-anti C-reactive protein monoclonal antibody conjugate manufactured by Example 2-2 above were added, then phosphate buffered saline (PBS, pH 7.4) was added thereto so as to have a final volume of 200 μl, and reacted for 30 minutes.

The reaction solution was sequentially passed through the film for flocculation (PDMS) and 0.8 μm MMM (asymmetric super-micron membrane) filtration membrane by the same method as Experimental Example 1-2 above, and captured to the membrane, and comparison in view of fluorescent signal was conducted.

Figure 10:
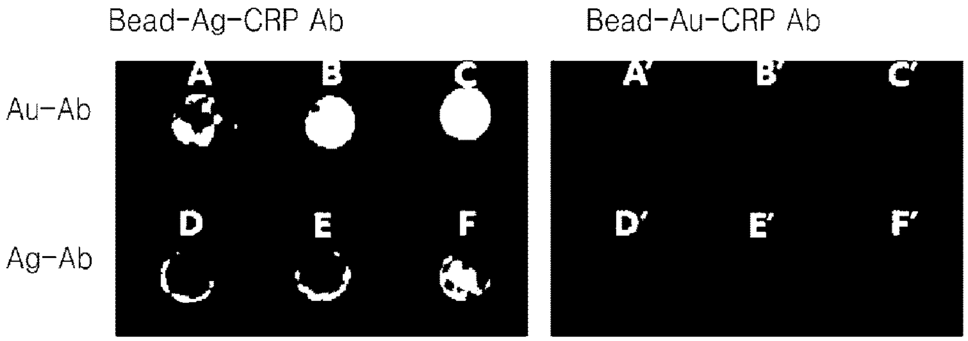
FIG. 10 shows results obtained by measuring CRP through fluorescent signal for each CRP concentration, using BSA protein-coated fluorescent latex bead-5×AgNP-anti-C-reactive protein pAb and BSA protein-coated fluorescent latex bead-5×AuNP-anti-C-reactive protein pAb according to an embodiment of the present invention (BSA protein-coated fluorescent latex bead-5×AgNP-anti-C-reactive protein pAb, BSA protein-coated fluorescent latex bead-5×AuNP-anti-C-reactive protein pAb+0 ug/ml(A,D,A',D'), 1 ug/ml(B,E,B',E'), 10 ug/ml(C,F,C',F')+AuNP-anti-C-reactive protein mAb, AgNP-anti-C-reactive protein mAb)

It could be confirmed from FIG. 10 that due to the AuNP-anti-CRP mAb conjugate, an intensity of fluorescent signal was increased, and in particular, at the time of reacting with the BSA protein coated LB(2 μm)-AgNP-anti-CRP pAb conjugate, intensity of the fluorescent signal was high. Accordingly, it could be appreciated that by the antibody immobilization method using the gold nanoparticle or the silver nanoparticle according to the present invention, the particle enables to be immobilized without limitation of a kind thereof.

Experimental Example 3-2

CRP Measurement Using Flow-Through-Hole (FTH) Membrane

Adsorption pads cut into a square shape and a double-sided tape having three holes therein were prepared, 0.8 μm MMM (asymmetric super-micron membrane) filtration membrane was placed onto the adsorption pad, the double-sided tape having holes was attached thereonto, 1 μl of BSA protein coated fluorescent LB(2 μm)-AgNP-anti-CRP pAb conjugate was loaded in each hole. After 10 μl of each of 0, 1 μg/ml and 10 μg/ml CRP antigens and 5 μl of AuNP-anti-CRP mAb were sequentially loaded, and a concentration of CRP was measured.

Figure 11:
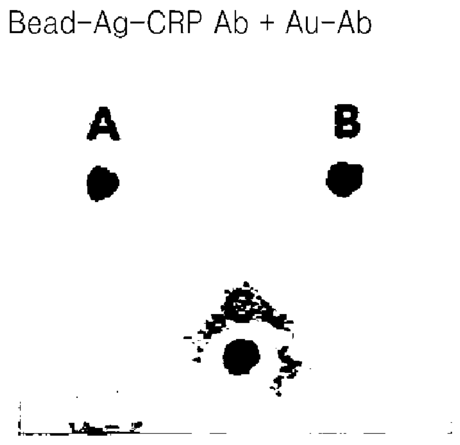
FIG. 11 shows results obtained by measuring CRP for each concentration, using BSA protein-coated fluorescent latex bead-5×AgNP-anti-C-reactive protein pAb according to an embodiment of the present invention (BSA protein-coated fluorescent latex bead-5×AgNP-anti-C-reactive protein pAb+0 ug/ml(A), 1 ug/ml(B), 10 ug/ml(C)+AuNP-anti-C-reactive protein mAb)

As shown in FIG. 11, it could be confirmed that as a concentration of CRP became increased, an amount of the BSA protein coated fluorescent LB(2 μm)-AgNP-anti-CRP pAb conjugate-CRP-AuNP-anti-CRP mAb complex remained on the filtration membrane was increased, wherein CPR concentration enabled to be measured using unique color of fluorescent latex bead and gold nanoparticle.

Experimental Example 3-3

CRP Measurement Using Lateral Flow Assay 0.3 μl of anti-mouse IgG Ab (control, 1 mg/ml) and anti-CRP pAb (1 mg/ml) as 2nd Ab were spotted on each of 180 sec nitrocelluolose (NC) film, and dried at room temperature for about 20 minutes. 10 μl of each 80 nm and 90 nm BSA protein coated magnetic nanoparticle ($Fe_3O_4$, $Fe_3O_4$—$SiO_2$)-gold nanoparticle-anti C-reactive protein monoclonal antibody conjugates manufactured by Example 1-1 above, 0, 10 ng/ml, 100 ng/ml and 1 μg/ml CRP antigens, each 1% of polyvinylpyrrolidone (PVP) and (surfactant 10G) were added, then CRP free serum (high purified) was added thereto so as to have a final volume of 100 μl, and a strip was slightly soaked into the mixture so that an end thereof contacted the mixture.

When an immune reaction was generated while the mixture moved along the strip, the immobilization state of the magnetic nanoparticle-gold nanoparticle-antibody conjugate was confirmed by observing whether or not signal was indicated. After the reaction was completed, the nitrocelluolose (NC) was washed by phosphate buffered saline (PBS, pH 7.4).

Figure 12:
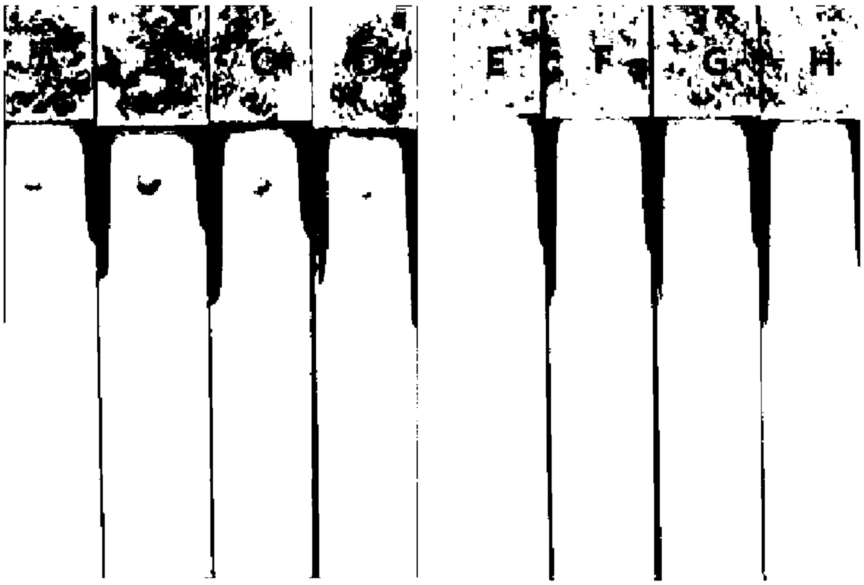
FIG. 12 shows results obtained by measuring CRP for each concentration, using each of 80 nm and 90 nm BSA protein-coated MNP ($Fe_3O_4$, $Fe_3O_4$—$SiO_2$)-5×AuNP-anti-C-reactive protein mAb by the immobilization method according to the present invention (0(A,E), 10 ng/ml(B,F), 100 ng/ml(C,G), 1 μg/ml(D,H) CRP+80 nm and 90 nm BSA protein-coated MNP ($Fe_3O_4$, $Fe_3O_4$—$SiO_2$)-5×AuNP-anti-C-reactive protein mAb)

As shown in FIG. 12, it could be confirmed that due to the immune reaction generated by the antibody immobilized to the nitrocelluolose (NC), the antigen, and the protein coated magnetic nanoparticle-gold nanoparticle-antibody conjugate, red signal was indicated by color of the nanoparticle of the conjugate regardless of the kind of the nanoparticle.

Experimental Example 4

H1N1 Virus Analysis Using BSA Protein-Coated Fluorescent Latex Bead (Fluorescent Red, LB)-Silver Nanoparticle (AgNP)-Antibody and Confirmation of Cross-Reaction with Other Sub-Type Virus

Experimental Example 4-1

H1N1 Analysis through Fluorescent Measurement $10^0$, $10^1$, $10^2$, $10^3$, $10^4$, and $10^5$ pfu of H1N1 virus were added to 1 μl of each BSA protein coated fluorescent latex bead (fluorescent Red, 2 μm LB)-silver nanoparticle (20 nm AgNP)-anti H1 virus monoclonal antibody (anti-H1 mAb) conjugate manufactured by Example 1-2 so as to have a final volume of 100 μl with PBS, followed by reaction for 20 minutes, and 1 μl of magnetic nanoparticle (MNP, CMX)-anti H1 virus monoclonal antibody (anti-H1 mAb) conjugate was added thereto, followed by reaction for 20 minutes.

100 μl of PBS solution was added to the reaction solution, then using magnetic at room temperature, the magnetic nanoparticle was separated from the solution for about 3 minutes to remove a supernatant, and 100 μl of PBS was added thereto, then using magnetic at room temperature, the magnetic nanoparticle was separated from the solution for about 3 minutes to remove a supernatant, 100 μl of PBS was added thereto, thereby collecting BSA protein-coated fluorescent LB(2 μm)-AgNP-anti-H1 mAb conjugate-H1N1 virus-MNP(CMX)-H1 mAb complex. After the above-described process was repeated once again, the solution was allowed to pass through 0.8 μm MMM (asymmetric super-micron membrane) filtration membrane by the same method as Experimental Example 1-2, then collected in the membrane, and fluorescent signal was confirmed.

Figure 13:
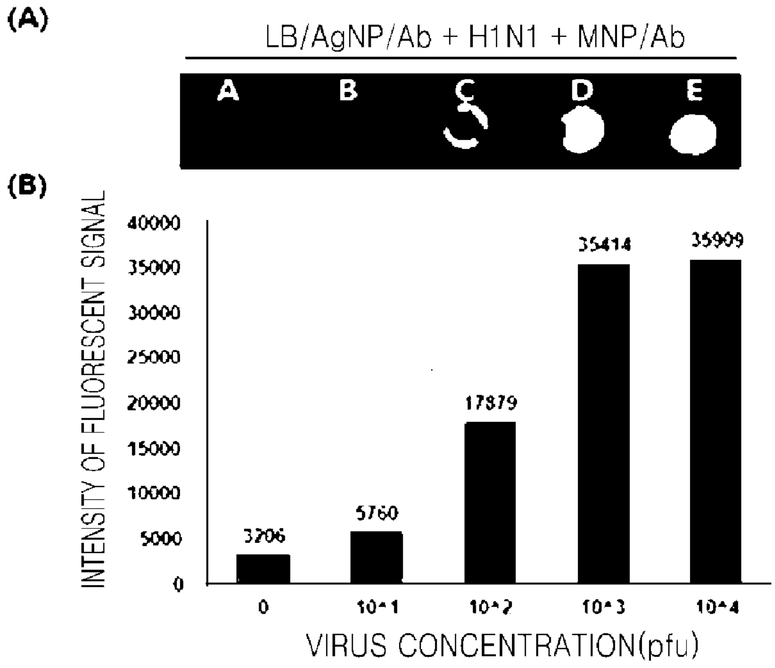
FIG. 13 shows results obtained by fluorescence for each H1N1 virus concentration, using BSA protein-coated fluorescent latex bead-5×AgNP-anti-H1 mAb, manufactured by using the immobilization method according to the present invention (BSA protein-coated fluorescent latex bead-5×AgNP-anti-H1 mAb+$10^0$ pfu(A), $10^1$ pfu(B), $10^2$ pfu(C), $10^3$ pfu(D)+$10^4$ pfu(E)+MNP(CMX)-H1 mAb)

In FIG. 13, (A) shows an image indicating virus and a fluorescent signal for each concentration and (B) is a graph showing a result obtained by measuring intensity of the fluorescent signal as a numerical value.

As shown in FIG. 13, as a concentration of H1N1 virus became increased, intensity of the fluorescent signal was increased and the measurement was achieved at up to $10^1$ pfu. It could be appreciated that since the fluorescent latex bead having immobilized antibody remained on the filtration membrane capturing microorganism by the silver nanoparticle reacted with the virus, the measurement was achieved by the fluorescent latex bead.

Experimental Example 4-2

Confirmation of Cross-Reaction with BSA Protein-Coated Fluorescent Latex Bead (Fluorescent Red, 2 μm LB)-Silver Nanoparticle (20 nm AgNP)-Anti H1 Virus Monoclonal Antibody (Anti-H1 mAb) Conjugate with Respect to Different Sub-type Virus In order to whether or not the multi-functional biomaterial conjugate according to the present invention enables to selectively detect the virus, 1 μl of magnetic nanoparticle (MNP, CMX)-anti-H1 monoclonal antibody (anti-H1 mAb) conjugate manufactured by Comparative Example 1 and $10^3$ pfu of each H1N1, H3N2 and H5N2 virus were added, then PBS was added thereto so as to have a final volume of 100 μl, and reacted for 20 minutes. The magnetic nanoparticle was separated from the reaction solution using magnetic at room temperature for about 3 minutes to remove a supernatant from the reaction solution, then 100 μl of PBS was added thereto and suspended.

1 μl of BSA protein coated fluorescent latex bead (fluorescent Red, 2 μm LB)-silver nanoparticle (20 nm AgNP)-anti H1 virus monoclonal antibody (anti-H1 mAb) conjugate manufactured by Example 1-2 was added to each solution, and reacted for 20 minutes. The magnetic nanoparticle was separated from the reaction solution using magnetic at room temperature for about 3 minutes to remove a supernatant from the reaction solution, then 100 μl of PBS was added to collect each MNP(CMX)-H1 mAb conjugate-virus-BSA protein coated fluorescent LB(2 μm)-AgNP-anti-H1 mAb complex. After the above-described process was repeated once again, the solution was allowed to pass through 0.8 μm CA(Cellulose Acetate membrane) filtration membrane by the same method as Experimental Example 4-1, then collected in the membrane, and fluorescent signal was confirmed.

Figure 14:
FIG. 14 shows results by confirming whether or not a cross-reaction is generated with different sub-type virus with respect to BSA protein-coated fluorescent latex bead-5×AgNP-anti-H1 mAb (BSA protein-coated fluorescent latex bead-5×AgNP-anti-H1 mAb+$10^0$ pfu(A), $10^3$ pfuH1N1(B), $10^3$ pfuH3N2(C), $10^3$ pfuH5N2(D)+MNP(CMX)-H1 mAb)

As a result, as shown in FIG. 14, it could be confirmed that in H3N2 and H5N2 which are different sub-type virus, fluorescent signal by BSA protein coated fluorescent LB(2 μm)-AgNP-anti-H1 mAb was not indicated, but in H1N1, fluorescent signal by BSA protein coated fluorescent LB(2 μm)-AgNP-anti-H1 mAb was selectively indicated.

Experimental Example 4-3

Confirmation of Cross-Reaction with BSA Protein Coated Fluorescent Latex Bead (Fluorescent Red, 2 μm LB)-Silver Nanoparticle (20 nm AgNP)-Anti H5 Virus Monoclonal Antibody (Anti-H5 mAb) Conjugate with Different Sub-type Virus The magnetic nanoparticle (MNP, CMX)-anti H5 monoclonal antibody (anti-H5 mAb) conjugate manufactured by Comparative Example 1 and the BSA protein coated fluorescent latex bead (fluorescent Red, 2 μm LB)-silver nanoparticle (20 nm AgNP)-anti H5 virus monoclonal antibody (anti-H5 mAb) manufactured by Example 1-2 were reacted with the different sub-type virus, that is, H1N1, H3N2 and H5N2, by Experimental Example 4-2, and then analyzed.

Figure 15:
FIG. 15 shows results by confirming whether or not a cross-reaction is generated with different sub-type virus with respect to BSA protein-coated fluorescent latex bead-5×AgNP-anti-H5 mAb (BSA protein-coated fluorescent latex bead-5×AgNP-anti-H5 mAb+$10^0$ pfu(A), $10^3$ pfuH1N1(B), $10^3$ pfuH3N2(C), $10^3$ pfuH5N2(D)+MNP(CMX)-H5 mAb)

As a result, as shown in FIG. 15, it could be confirmed that in H1N1 and H3N2, fluorescent signal by BSA protein coated fluorescent LB (2 μm)-AgNP-anti-H5 mAb was not indicated, but in H5N2, fluorescent signal by BSA protein coated fluorescent LB (2 μm)-AgNP-anti-H5 mAb was selectively indicated.

Experimental Example 5

Isolation of T Cell (CD3) Using BSA Protein Coated Undyed Latex Beads (LB)-Gold Nanoparticle (AuNP)-Antibody

Experimental Example 5-1

Figure 16:
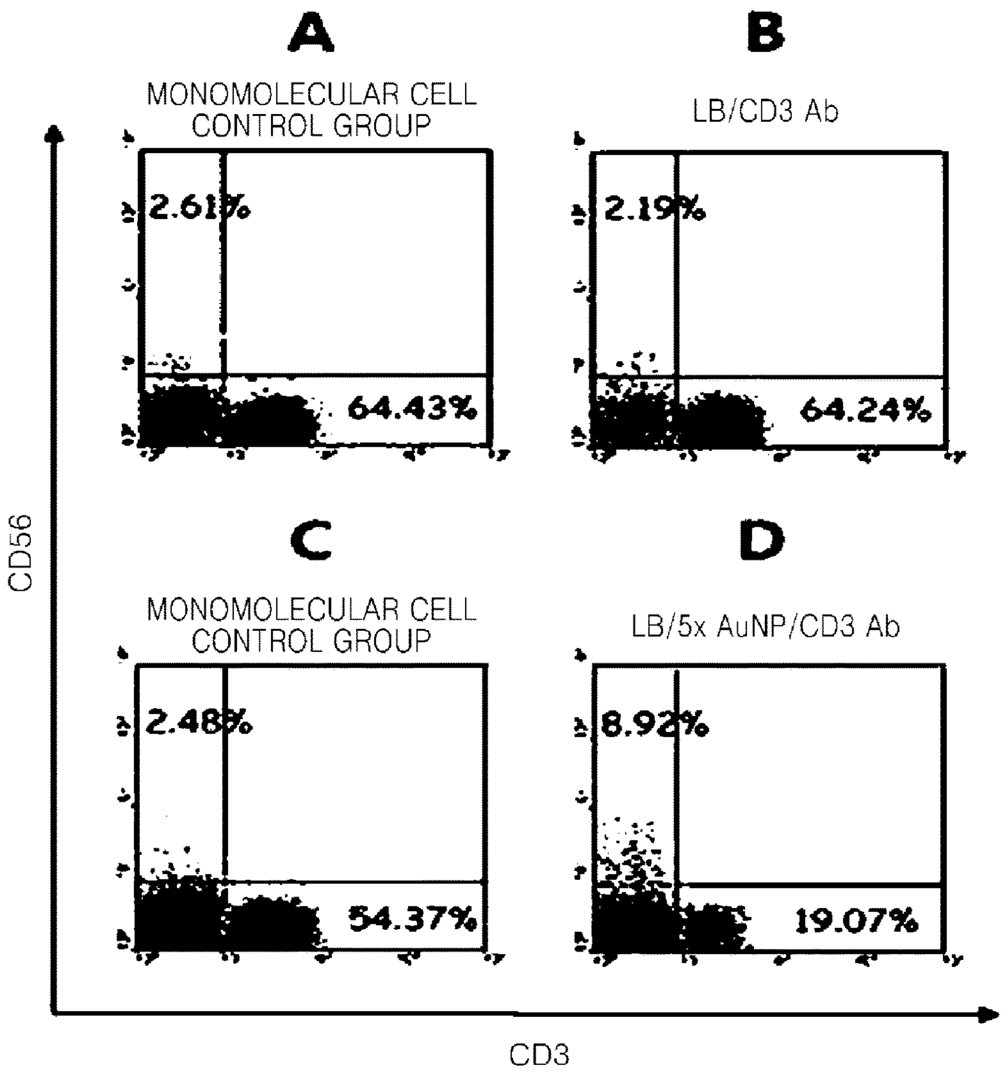
FIG. 16 shows results obtained by confirming T cell isolation rate in a mononuclear cell of blood, using undyed latex bead-anti-human CD3Ab to which an antibody is immobilized without using a silver (Ag) nanoparticle and undyed latex bead-5×AgNP-anti-human CD3 Ab to which an antibody is immobilized by using a silver nanoparticle (control(A), undyed latex bead-anti-human CD3Ab(B), control(C), undyed BSA protein-coated latex bead-5×AgNP-anti-human CD3 Ab(D)+blood)

Confirmation of Immobilization Efficiency of Antibody by T cell Isolation Rate Each of the undyed latex bead, 0.9 μm (LB)-anti human CD3 antibody (anti-human CD3 Ab) conjugate manufactured by Comparative Example 2 and the BSA protein coated undyed latex bead, 0.9 μm (LB)-gold nanoparticle, 20 nm (AuNP)-anti human CD3 antibody (anti-human CD3Ab) manufactured by Example 1-2 was mixed with blood, and left for 20 minutes. 2% FBS-PBS having the same volume was added to the reaction solution and mixed well, then placed onto density medium(Ficoll), followed by centrifugation at room temperature under conditions of 2,000 rpm and break off. After centrifugation, cell positioned in the boundary of density medium plasma of Ficoll was collected, and whether or not T cell (CD3) is formed and selective isolation rate (removal) of T cell (CD3) were confirmed by FACS, thereby confirming an effect of the method for immobilizing the antibody to the latex bead using the gold nanoparticle. As shown in FIG. 16, it could be confirmed that at the time of using the BSA protein coated latex bead (LB)-gold nanoparticles (AuNP)-antibody conjugate, the isolation (removal) efficiency of T cell (CD3) was higher than that of the method for directly immobilizing the antibody to the latex bead, thereby confirming that the antibody immobilization efficiency was increased.

Experimental Example 6

Figure 17:
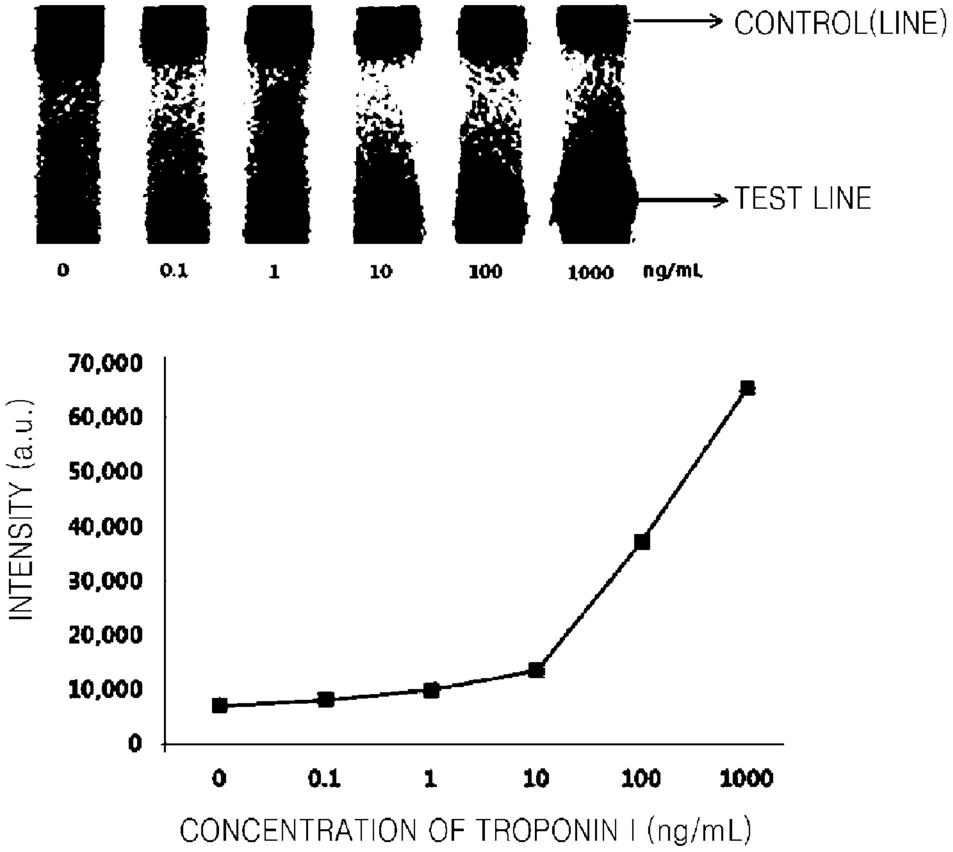
FIG. 17 shows analysis results of Troponin I obtained by using a HRP-coated gold (Au) nanoparticle-gold nanoparticle antibody conjugate and combination of later-flow assay strip and chemiluminescent method.

Troponin I Analysis Using HRP Coated Gold Nanoparticle-Gold Nanoparticle Antibody Conjugate Anti Mouse IgG antibody (Control line) and Troponin I antibody (Test line) were applied onto a nitrocellulose membrane using Dispensor (Zeta) by 8 mm at a concentration of 0.1 mg/ml. The applied nitrocellulose membrane was cut into an interval of 3.8 mm to manufacture strip sensors (the coated amount of the antibody for each sensor=38 ng/strip). In order to measure Troponin I for each concentration, the HRP coated gold nanoparticle-gold nanoparticle antibody conjugate manufactured by Example 1-3 was added to a human serum (Sigma Co.) solution containing 1×, 2% polyvinylpyrrolidone(PVP) (Sigma Co.) and 2% Surfactate 10G(Fitzgerald) and mixed with Troponine I at a concentration of 0 to 1000 ng/ml and each mixture was put into 96 well plate, and then the manufactured strip sensor was put thereinto, followed by reaction for 10 minutes. After the reaction was completed, the strip was put into 96 well plate containing PBS buffer again and washed for 20 minutes. After the washing was completed, sample pad of the strip was removed, and then the strip was treated with 20 μl of 0.1 M Tris-HCl(pH 8.8) buffer into which 2 mM luminol (Sigma Co.), 0.5 mM p-coumaricacid(Sigma Co.), and 2 mM hydrogen peroxide were dissolved. Then, chemiluminescent signal was measured for 120 seconds using ChemiDoc(Bio-Rad), and results thereof were shown in FIG. 17. As shown in test line of FIG. 17, it was confirmed that the signal was increased by an increase in a concentration within the range of the concentration of 0.1 to 1,000 ng/ml of Troponin I.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

INDUSTRIAL APPLICABILITY

According to the present invention, the method for manufacturing the multi-functional bio-material conjugate may prevent precipitation of nanoparticles, easily immobilize a bio-material, and manufacture a bio-material conjugate having multiple functions, by using two kinds of particles. In addition, the multi-functional bio-material conjugate manufactured by the present method may be used to detect microorganisms at up to a concentration of $10^1$ cfu.

The invention claimed is:

1. A method for manufacturing a bio-material conjugate, the method comprising:

coating a first nanoparticle with a protein, wherein the first nanoparticle has magnetic or fluorescent characteristics, and the first nanoparticle is surface-modified with carboxylic acid;

adsorbing a second nanoparticle having metallic characteristics onto the protein; and adsorbing a bio-material onto the second nanoparticle, wherein the first nanoparticle has a size larger than that of the second nanoparticle, the first nanoparticle has a size of 80 nanometers (nm) to 500 nm, the first nanoparticle is at least one of a latex nanoparticle or a magnetic nanoparticle, the protein is at least one selected from bovine serum albumin (BSA) or horseradish peroxidase (HRP), and the bio-material is an antibody.

2. The method of claim 1, wherein the second nanoparticle is selected from the group consisting of gold, silver, copper, and platinum.

3. A bio-material conjugate comprising:

a first nanoparticle coated with a protein, wherein the first nanoparticle has magnetic or fluorescent characteristics, and the first nanoparticle is surface-modified with carboxylic acid;

a second nanoparticle having metallic characteristics and adsorbed on the protein; and a bio-material adsorbed onto the second nanoparticle, wherein the first nanoparticle has a size larger than that of the second nanoparticle, the first nanoparticle has a size of 80 nanometers (nm) to 500 nm, the first nanoparticle is at least one of a latex nanoparticle or a magnetic nanoparticle, the protein is at least one selected from bovine serum albumin (BSA) or horseradish peroxidase (HRP), and the bio-material is an antibody.

4. The bio-material conjugate of claim 3, wherein the second nanoparticle is selected from the group consisting of gold, silver, copper, and platinum.

5. A biosensor comprising the bio-material conjugate of claim 3.

6. The method of claim 1, wherein coating the first nanoparticle comprises coating an entire outer surface modified with carboxylic acid of the first nanoparticle with the protein.

7. The bio-material conjugate of claim 3, wherein an entire outer surface of the first nanoparticle is coated with the protein.

8. The method of claim 1, wherein the second nanoparticle has a size of 5 to 100 nm.

9. The bio-material conjugate of claim 3, wherein the second nanoparticle has a size of 5 to 100 nm.

* * * * *